US00PP17443P3

(12) United States Plant Patent
Meilland

(10) Patent No.: US PP17,443 P3
(45) Date of Patent: Feb. 27, 2007

(54) SHRUB ROSE PLANT NAMED 'MEIGADRAZ'

(50) Latin Name: *Rosa hybrida*
Varietal Denomination: Meigadraz

(75) Inventor: Alain A. Meilland, Antibes (FR)

(73) Assignee: CP Delaware, Inc., Wilmington, DE (US)

( * ) Notice: Subject to any disclaimer, the term of this patent is extended or adjusted under 35 U.S.C. 154(b) by 14 days.

(21) Appl. No.: 11/000,914

(22) Filed:
Dec. 2, 2004

(65) Prior Publication Data

US 2005/0091719 P1 Apr. 28, 2005

(51) Int. Cl.
*A01H 5/00* (2006.01)

(52) U.S. Cl. ..... Plt./102

(58) Field of Classification Search ..... Plt./102, Plt./107, 108
See application file for complete search history.

(56) References Cited

PUBLICATIONS

Meilland International: A World of Roses [online], [retrieved on Jan. 9, 2006]. Retrieved from the Internet <http://www.meilland.com/xmain/2middle.html>.*

UPOV–ROM GTITM, Plant Variety Database, 2005/04, GTI Jouve Retrieval Software, Citation for *Rosa* 'Meigadraz'.*

* cited by examiner

*Primary Examiner*—Kent Bell
*Assistant Examiner*—June Hwu
(74) *Attorney, Agent, or Firm*—Buchanan Ingersoll & Rooney PC

(57) ABSTRACT

A new and distinct variety of landscape shrub rose plant is provided which forms in abundance on a substantially continuous basis attractive red-purple blossoms commonly bearing approximately 13 to 15 petals. The new variety is a spontaneous mutation of unknown causation of the 'Radrazz' variety (U.S. Plant Pat. No. 11,836) that forms vivid red blossoms which commonly display approximately 10 petals. The vegetation is vigorous and the growth habit is bushy and rounded. The foliage is very ornamental, dark green, and semi-glossy and contrasts nicely with the red-purple blossom coloration. Excellent resistance to blackspot is displayed. The new plant is particularly well suited for pot forcing under greenhouse growing conditions to form an attractive gift plant.

1 Drawing Sheet

Figure 1:
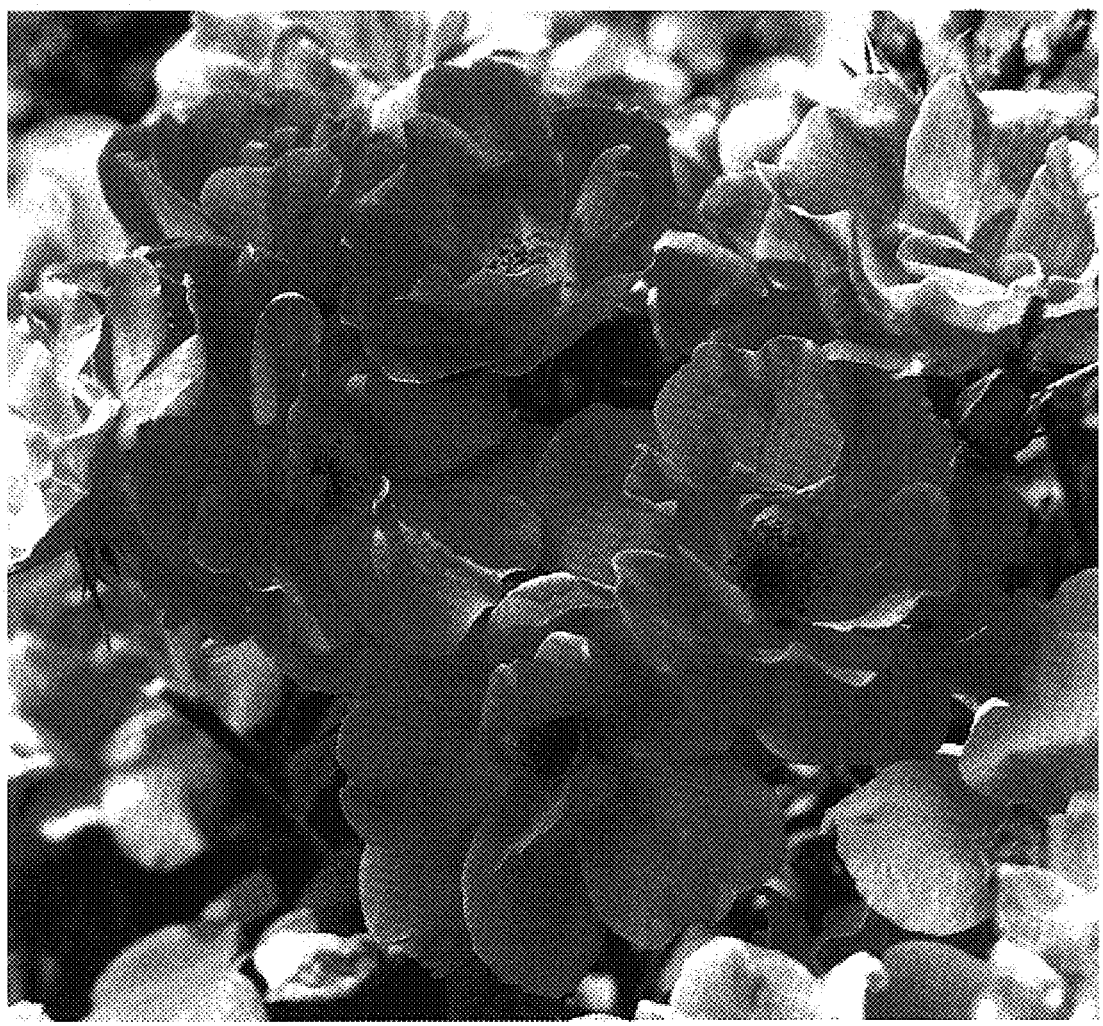

Botanical/commercial classification: *Rosa hybrida*/Shrub Rose Plant.
Varietal denomination: cv. Meigadraz.

SUMMARY OF THE INVENTION

The new variety of *Rosa hybrida* landscape shrub rose plant of the present invention was discovered as a branch mutation during June 2000 while growing among a block of rose plants of the 'Radrazz' variety (U.S. Plant Pat. No. 11,836) growing outdoors at Le Cannet des Maures, Var, France. I was attracted to the new variety primarily because of its distinctive red-purple blossom coloration that was unlike that of the parental variety. The new variety is believed to be a spontaneous naturally-occurring mutation of the 'Radrazz' variety of unknown causation. Had I not discovered and preserved the original plant of the new variety it would have been lost to mankind.

It was found that the new variety of landscape shrub rose plant of the present invention possesses the following combination of characteristics:

(a) abundantly and substantially continuously forms attractive red-purple blossoms commonly bearing approximately 13 to 15 petals on average unlike the vivid red blossoms of the 'Radrazz' variety (U.S. Plant Pat. No. 11,836), (b) exhibits a bushy and rounded growth habit, (c) forms vigorous vegetation, (d) forms attractive very ornamental dark green semi-glossy foliage, and (e) displays excellent resistance to blackspot.

The new rose variety has a propensity for everblooming combined with blackspot resistance.

The new variety of the present invention can be readily distinguished from the parental 'Radrazz' variety through an inspection of the blossoms. More specifically, the new variety displays red-purple blossoms having approximately 13 to 15 petals on average rather than vivid red blossoms having approximately 10 petals on average that are displayed by the parental 'Radrazz' variety. Also, the new variety of the present invention readily also can be distinguished from the 'Radyod' variety (U.S. Plant Pat. No. 14,700) and the 'Radcon' variety (U.S. Plant Pat. No. 15,070) which are other mutations of the 'Radrazz' variety. More specifically, the blossoms of the 'Radyod' variety are light pink, and the blossoms of the 'Radcon' variety a darker pink than those of the 'Radyod' variety. The blossoms of the new variety of the present invention are more red-purple, and commonly possess more petals than the blossoms of the 'Radyod' variety.

The new variety well meets the needs of the horticultural industry, and is particularly well suited for pot forcing under greenhouse growing conditions to form an attractive gift plant. The red-purple blossoms contrast nicely with the semi-glossy dark green foliage.

The characteristics of the new variety have been found at Le Cannet des Maures, Var, France, to be homogeneous and stable and are strictly transmissible by asexual propagation such as budding, grafting, and the use of cuttings from one generation to another carried out at such location.

The new variety has been named the 'Meigadraz' variety.

BRIEF DESCRIPTION OF THE PHOTOGRAPH

The accompanying photograph of FIG. 1 shows, as nearly true as it is reasonably possible to make the same in a color illustration of this character, a typical specimen showing the attractive red-purple flowers of the new variety at various stage of maturity. The rose plants were approximately two years of age and were grown in the ground outdoors on *Rosa froebelii* rootstock at Le Cannet des Maures, Var, France.

DETAILED DESCRIPTION

The chart used in the identification of the colors is that of The Royal Horticultural Society (R.H.S. Colour Chart). The description is based on approximately two year-old specimens of the new variety during October while grown outdoors on *Rosa froebelii* rootstock at Le Cannet des Maures, Var, France.

Class: Landscape Shrub Rose.

Plant:

*Height.*—Approximately 50 to 60 cm on average at the end of the growing season.

*Width.*—Approximately 50 to 60 cm on average at the end of the growing season.

*Habit.*—Bushy and rounded.

Branches:

*Color.*—Young stems: near Yellow-Green Group 144B suffused with Red Group 53D. Adult wood: near Yellow-Green Group 146C.

*Texture.*—Young stems: smooth. Adult wood: smooth.

*Thorns.*—Quantity: commonly approximately 6 on average on 15 cm of young stems, and approximately 5 on average on 15 cm of adult stems. Size: approximately 1 to 1.5 cm in length on average on young stems and on adult stems. Configuration: longish pointed, possess an oval base, curved downwards on the upper surface, and concave on the under surface. Color: on young stems near Yellow-Green Group 146C and widely suffused with Greyed-Purple Group 184A, and on adult stems near Greyed-Orange Group 166B and 166C.

Leaves:

*Length.*—Approximately 11 cm on average.

*Width.*—Approximately 8 cm on average.

*Leaflets.*—Number: 3, 5, and 7 (most often). Shape: possess an obtuse base, and an acuminate tip. Size: the terminal leaflet is approximately 5 cm in length on average and approximately 2.6 cm in width on average. Margin: single and fine serration. Texture: smooth. Overall appearance: very dense, dark green in coloration, and with a semi-glossy aspect on the upper surface. Color (new foliage): Upper surface: near Yellow-Green Group 147A suffused with Red Group 47A. Under surface: near Yellow-Green Group 147B. Color (adult foliage): Upper surface: near Yellow-Green Group 147A. Under surface: near Yellow-Green Group 147B. Petioles: the petiole typically is approximately 1.2 cm in length on average on the terminal leaflet, on the upper surface near Yellow-Green Group 144A with some highlights of Greyed-Purple Group 184A and non-glandular, and on the under surface near Yellow-Green Group 144A and with a very few prickles. Stipules: typically approximately 1 to 1.2 cm in length on average, typically approximately 0.4 cm in width on average, adnate, pectinate, rather broad, and near Green Group 137C on the upper surface, and near Green Group 137D on the under surface.

Inflorescence:

*Number flowers.*—Commonly approximately 6 to 15 blooms on average per stem.

*Peduncle.*—Length: typically approximately 2.5 cm on average. Diameter: typically approximately 0.2 cm on average. Strength: relatively strong. Texture: typically covered with small prickles. Color: near Yellow-Green Group 144A.

*Sepals.*—Length: typically approximately 2 to 2.8 cm on average. Width: typically approximately 0.6 cm at the widest point on average. Configuration: slender and pointed with a few foliaceous appendages. Number: five. Texture: the upper surface commonly is tomentose, and the under surface commonly is glandular. Color (upper surface): near Green Group 138C. Color (under surface): near Green Group 137B and 137C.

*Buds.*—Length: commonly approximately 1 to 1.5 cm on average. Width: commonly approximately 1 cm on average. Size: medium. Shape: elongated. Color (upper surface): near Red-Purple Group 57A and 57B. Color (under surface): near Red-Purple Group 68B and lightly suffused with Red-Purple Group 68A. Color (basal petal spot): near Yellow Group 3D.

*Flower.*—Arrangement: imbricated petals. Diameter: approximately 7 to 8 cm on average. Shape: flat cup-shaped. Fragrance: none. Petal form: cuneiform with a reflected apex. Petal number: approximately 13 to 15 on average under normal growing conditions. Petal length: commonly approximately 3 cm on average. Petal width: commonly approximately 2.4 cm on average. Color during course of opening: Upper surface: near Red-Purple Group 57D, widely suffused with Red-Purple Group 67C, and lightly suffused with Red-Purple Group 57B. Under surface: near Red-Purple Group 68B and lightly suffused with Red-Purple Group 68A. Basal petal spot: near Yellow Group 3D. Color when open: Upper surface: near Red-Purple Group 68C suffused with Red-Purple Group 68B. Under surface: near Red-Purple Group 68D suffused with Red-Purple Group 68B. Basal petal spot: near White Group 155D on the upper and under surfaces. Petal texture: smooth. Petaloids: none observed. Anthers: commonly 121 in number on average, approximately 0.1 cm in size on average, and near Yellow Group 13D in coloration. Pollen: present and near Yellow Group 13D in coloration. Filaments: typically approximately 121 on average; regularly arranged around the styles, commonly approximately 0.6 to 0.8 cm in length, and near Red Group 42C in coloration. Stigmas: typically approximately 0.1 cm in size, and near Yellow Group 13D in coloration. Styles: typically approximately 32 on average; typically approximately 0.2 cm in length on average, and near Red Group 42C in coloration. Receptacle: funnel-shaped, slightly glandular on the surface, approximately 1 cm in length on average and approximately 0.8 cm in width on average, and near Green Group 137C in coloration.

Lasting quality: commonly approximately two weeks on the plant. Petal drop: very good with the petals commonly dropping cleanly before drying. Hips: formed in a sparse quantity and commonly lack seeds, narrow pear-shaped in configuration, commonly approximately 1 cm in length on average, approximately 0.8 cm in width at the widest point, commonly bear a few prickles, and near Green Group 137D in coloration.

Development:

*Vegetation.*—Vigorous and strong.

*Blossoming.*—Abundant and substantially continuous.

*Resistance to diseases.*—Excellent with respect to blackspot.

*Propensity to form hips.*—Sparsely formed.

*Resistance to cold.*—Has performed well in U.S.D.A. Hardiness Zone Nos. 4A and 4B.

*Resistance to heat.*—Has maintained active vegetation and blooming capacity during the summer in U.S.D.A. Hardiness Zone Nos. 8A and 8B.

What is claimed is:

1. A new and distinct landscape shrub rose plant which exhibits the following combination of characteristics:

(a) abundantly and substantially continuously forms attractive red-purple blossoms commonly bearing approximately 13 to 15 petals on average unlike the vivid red blossoms of the 'Radrazz' variety (U.S. Plant Pat. No. 11,836), (b) exhibits a bushy and rounded growth habit, (c) forms vigorous vegetation, (d) forms attractive very ornamental dark green semi-glossy foliage, and (d) displays excellent resistance to blackspot;

substantially as illustrated and described.

* * * * *